US011285439B2

(12) United States Patent
Denny et al.

(10) Patent No.: US 11,285,439 B2
(45) Date of Patent: Mar. 29, 2022

(54) COMPLEXATION AND REMOVAL OF MERCURY FROM FLUE GAS DESULFURIZATION SYSTEMS

(71) Applicant: ECOLAB USA INC., St. Paul, MN (US)

(72) Inventors: Nicholas R. Denny, Glen Ellyn, IL (US); Bruce A. Keiser, Plainfield, IL (US); David M. Dotzauer, St. Paul, MN (US); Wayne M. Carlson, Batavia, IL (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 16/156,477

(22) Filed: Oct. 10, 2018

(65) Prior Publication Data

US 2019/0039019 A1    Feb. 7, 2019

Related U.S. Application Data

(63) Continuation of application No. 15/241,259, filed on Aug. 19, 2016, now Pat. No. 10,124,290.

(60) Provisional application No. 62/208,117, filed on Aug. 21, 2015.

(51) Int. Cl.
| | |
|---|---|
| *B01D 53/64* | (2006.01) |
| *A61L 2/20* | (2006.01) |
| *A61L 101/20* | (2006.01) |
| *A61L 101/36* | (2006.01) |
| *B01D 53/78* | (2006.01) |
| *B01D 53/50* | (2006.01) |

(52) U.S. Cl.
CPC .............. *B01D 53/64* (2013.01); *A61L 2/208* (2013.01); *B01D 53/78* (2013.01); *A61L 2101/36* (2020.08); *B01D 53/502* (2013.01); *B01D 2251/108* (2013.01); *B01D 2251/304* (2013.01); *B01D 2251/404* (2013.01); *B01D 2251/70* (2013.01)

(58) Field of Classification Search
None
See application file for complete search history.

(56) References Cited

U.S. PATENT DOCUMENTS

| | | |
|---|---|---|
| 4,107,271 A | 8/1978 | Atsukawa et al. |
| 5,494,588 A | 2/1996 | LaZonby |
| 5,658,467 A | 8/1997 | LaZonby et al. |
| 5,658,540 A | 8/1997 | Valentino |
| 5,733,786 A | 3/1998 | Green |
| 5,785,867 A | 7/1998 | LaZonby et al. |
| 5,980,758 A | 11/1999 | LaZonby et al. |
| 6,007,726 A | 12/1999 | Yang et al. |
| 6,015,536 A * | 1/2000 | Lokkesmoe ........... B01D 53/38 423/210 |
| 6,123,870 A | 9/2000 | Yang et al. |
| 6,136,205 A | 10/2000 | Dallmier et al. |
| 6,156,229 A | 12/2000 | Yang et al. |
| 6,214,304 B1 | 4/2001 | Rosenthal et al. |
| 6,245,729 B1 | 6/2001 | Wei et al. |
| 6,270,722 B1 | 8/2001 | Yang et al. |
| 6,287,473 B1 | 9/2001 | Yang et al. |
| 6,319,888 B2 | 11/2001 | Wei et al. |
| 6,423,267 B1 | 7/2002 | Yang et al. |
| 6,503,470 B1 | 1/2003 | Nolan et al. |
| 6,669,904 B1 | 12/2003 | Yang et al. |
| 6,808,692 B2 | 10/2004 | Oehr |
| 6,942,840 B1 * | 9/2005 | Broderick .............. B01D 53/64 210/914 |
| 7,514,053 B2 * | 4/2009 | Johnson ............. B01D 53/1456 423/210 |
| 7,722,843 B1 | 5/2010 | Srinivasachar |
| 8,080,088 B1 | 12/2011 | Srinivasachar |
| 8,110,163 B2 | 2/2012 | Keiser et al. |
| 8,142,548 B2 | 3/2012 | Higgins et al. |
| 8,173,566 B2 | 5/2012 | Olson et al. |
| 8,309,046 B2 | 11/2012 | Pollack et al. |
| 8,679,430 B2 | 3/2014 | Pollack et al. |
| 8,729,296 B2 | 5/2014 | Fast et al. |
| 8,865,099 B1 | 10/2014 | Gray et al. |

(Continued)

FOREIGN PATENT DOCUMENTS

| | | |
|---|---|---|
| CL | 201100611 | 3/2011 |
| CL | 201100612 | 3/2011 |

(Continued)

OTHER PUBLICATIONS

International Search Report and Written Opinion for International Application No. PCT/US2016/047836, 13 pages, (dated Nov. 23, 2016).
International Search Report and Written Opinion for International Application No. PCT/US2016/047822, 12 pages, (dated Nov. 23, 2016).
International Search Report and Written Opinion for International Application No. PCT/US2016/047830, 13 pages (dated Nov. 27, 2016).
International Search Report and Written Opinion for International Application No. PCT/US2018/040690, 17 pages (dated Nov. 9, 2018).

(Continued)

*Primary Examiner* — Sheng H Davis
(74) *Attorney, Agent, or Firm* — Eric D. Babych; Barnes & Thornburg LLP

(57) ABSTRACT

A method for the reduction and prevention of mercury emissions into the environment from combusted fossil fuels or other off-gases with the use of peracetic acid is disclosed. The peracetic acid is used for the capture of mercury from the resulting flue gases using a flue gas desulfurization system or scrubber. The method uses peracetic acid in conjunction with a scrubber to capture mercury and lower its emission and/or re-emission with stack gases. The method allows the use of coal as a cleaner and environmentally friendlier fuel source as well as capturing mercury from other processing systems.

17 Claims, 1 Drawing Sheet

(56) References Cited

U.S. PATENT DOCUMENTS

| | | |
|---|---|---|
| 8,877,254 B2 | 11/2014 | Li et al. |
| 9,603,963 B2 | 3/2017 | Temple |
| 2002/0068030 A1 | 6/2002 | Nolan et al. |
| 2002/0102189 A1 | 8/2002 | Madden et al. |
| 2003/0143214 A1 | 7/2003 | Pellico et al. |
| 2003/0161771 A1 | 8/2003 | Oehr |
| 2003/0170159 A1 | 9/2003 | Honjo et al. |
| 2003/0200997 A1 | 10/2003 | Gill et al. |
| 2005/0244319 A1 | 11/2005 | Hurley |
| 2006/0021506 A1* | 2/2006 | Hakka .......... B01D 53/507 95/129 |
| 2006/0048646 A1 | 3/2006 | Olson et al. |
| 2006/0210463 A1 | 9/2006 | Comrie |
| 2007/0184394 A1 | 8/2007 | Comrie |
| 2008/0286183 A1 | 11/2008 | Radway |
| 2009/0148372 A1 | 6/2009 | Keiser et al. |
| 2010/0061909 A1* | 3/2010 | Kawamura ...... B01D 53/1456 423/243.02 |
| 2011/0123422 A1 | 5/2011 | Wang |
| 2011/0250110 A1 | 10/2011 | Keiser et al. |
| 2011/0268637 A1 | 11/2011 | Ukai et al. |
| 2012/0090517 A1 | 4/2012 | Radway |
| 2012/0100053 A1 | 4/2012 | Durham et al. |
| 2012/0189520 A1* | 7/2012 | Pfeffer ............ B01J 19/26 423/235 |
| 2013/0034485 A1 | 2/2013 | Naito |
| 2013/0109191 A1* | 5/2013 | Le Tiec ........ H01L 21/02057 438/752 |
| 2013/0168293 A1 | 7/2013 | O'Rear et al. |
| 2013/0180923 A1* | 7/2013 | Keiser ............ B01D 53/96 210/662 |
| 2013/0224093 A1 | 8/2013 | Xiong et al. |
| 2013/0306521 A1 | 11/2013 | O'Rear et al. |
| 2013/0309157 A1 | 11/2013 | Sjostrom et al. |
| 2013/0330257 A1 | 12/2013 | Tramposch |
| 2014/0079615 A1 | 3/2014 | Honjo et al. |
| 2014/0178249 A1* | 6/2014 | Tichy ............ A01N 37/16 422/28 |
| 2014/0224121 A1 | 8/2014 | Mimna et al. |
| 2015/0068189 A1 | 3/2015 | Sawatsubashi et al. |
| 2015/0096480 A1 | 4/2015 | Comrie |
| 2015/0265967 A1 | 9/2015 | Butz et al. |
| 2015/0283500 A1 | 10/2015 | Butz et al. |
| 2016/0158701 A1 | 6/2016 | Brown et al. |
| 2017/0050144 A1 | 2/2017 | Kamiyama et al. |

FOREIGN PATENT DOCUMENTS

| | | |
|---|---|---|
| CL | 2012003022 A1 | 6/2013 |
| CL | 2013001404 A1 | 12/2013 |
| CL | 2013001683 A1 | 12/2013 |
| CL | 2013002717 A1 | 1/2014 |
| CL | 2013000923 A1 | 10/2014 |
| CL | 2018000417 A1 | 7/2018 |
| CL | 2018000419 A1 | 7/2018 |
| CN | 1864813 A | 11/2006 |
| CN | 1962034 A | 5/2007 |
| CO | 6620057 A2 | 2/2013 |
| EP | 1059112 A2 | 12/2000 |
| JP | H05220345 A | 8/1993 |
| WO | WO 03/076051 A1 | 9/2003 |
| WO | WO 2007/149867 A1 | 12/2007 |
| WO | 2008008475 A2 | 1/2008 |
| WO | WO 2009/043108 A1 | 4/2009 |
| WO | WO 2009/052362 A2 | 4/2009 |
| WO | WO 2011/127323 A2 | 10/2011 |
| WO | WO 2013/188327 A1 | 12/2013 |
| WO | 2014031623 A1 | 2/2014 |
| WO | 2014082076 A1 | 5/2014 |
| WO | WO 2014/126749 A1 | 8/2014 |
| WO | 2014150217 A1 | 9/2014 |
| WO | WO 2017/034999 A1 | 3/2017 |
| WO | WO 2017/037454 A1 | 3/2017 |

OTHER PUBLICATIONS

Krzyżyńska, Renata, et al., "Absorption of NOx, SO2, and Mercury in a Simulated Additive-Enhanced Wet Flue Gas Desulphurization Scrubber," Polish J. of Environ. Stud., 19(6):1255-1262 (2010).

Miller, Charles E., et al., "Mercury Capture and Fate Using Wet FGD at Coal-Fired Power Plants," DOE/NETL Mercury and Wet FGD R&D, pp. 1-37 (Aug. 2006).

Walsh, Jr., Williams A., et al., "Cost-effective retrofitting of fossil fueled power plants with pre-oxidation of raw flue gas to meet nitrogen oxides, sulfur oxides and mercury emission limits," 25th Annual International Pittsburgh Coal Conference, PCC—Proceedings, 2008, ISBN-10: 189097725X, ISBN-13: 9781890977252, Abstract only (2008).

* cited by examiner

COMPLEXATION AND REMOVAL OF MERCURY FROM FLUE GAS DESULFURIZATION SYSTEMS

TECHNICAL FIELD

This invention relates to the reduction of mercury emissions into the environment from the combustion of coal and/or other carbon-based fuels as well as from other processing systems. The invention relates to the method of capturing mercury from flue gases by flue gas desulfurization systems or scrubbers thereby reducing the levels of toxic mercury, which enables the use of coal as a clean and environmentally friendlier fuel source as well as makes other processing systems more environmentally desirable.

BACKGROUND

The demand for electricity continues to grow globally. In order to keep stride with the growing demand, coal continues to be a primary source for electricity generation. The burning of coal in power generation plants results in the release of energy, as well as the production of solid waste such as bottom and fly ash, and flue gas emissions into the environment. Emissions Standards, as articulated in The Clean Air Act Amendments of 1990 as established by the U.S. Environmental Protection Agency (EPA), requires the assessment of hazardous air pollutants from utility power plants.

Conventional coal-fired combustion furnaces and similar devices produce emissions that include pollutants such as mercury. Mercury vapor can contribute to health concerns. At the levels common in the atmosphere, the concentrations of mercury are usually safe. However, mercury can accumulate in ecosystems, for example, as a result of rainfall. Some conventional systems attempt to control mercury emissions with particulate collection devices.

The primary gas emissions are criteria pollutants (e.g., sulfur dioxide, nitrogen dioxides, particulate material, and carbon monoxide). Secondary emissions depend on the type of coal or fuel being combusted but include as examples mercury, selenium, arsenic, and boron. Coal-fired utility boilers are known to be a major source of anthropogenic mercury emissions in the United States. In December of 2000, the EPA announced its intention to regulate mercury emissions from coal-fired utility boilers despite the fact that a proven best available technology (BAT) did not exist to capture or control the levels of mercury released by the combustion of coal. This has been further complicated by the lack of quick, reliable, continuous monitoring methods for mercury.

Mercury (elemental symbol Hg) is a metal that melts at 234K (−38° F.) and boils at 630K (674° F.). As such, it can be expected to have a high vapor pressure relative to many metals. The oxidized forms of mercury, $Hg^{2+}$ and $Hg^+$, have much lower vapor pressures and can be captured by fly ash particulates.

Mercury is found in coals at concentrations ranging from 0.02 to 1 ppm. The mercury is present as sulfides or is associated with organic matter. Upon combustion the mercury is released and emitted into the flue gas as gaseous elemental mercury and other mercury compounds. The mercury appears in the flue gas in both the solid and gas phases (particulate-bound mercury and vapor-phase mercury, respectively). The so-called solid-phase mercury is really vapor-phase mercury adsorbed onto the surface of ash and/or carbon particles. The solid-phase mercury can be captured by existing particle control devices (PCDs) such as electrostatic precipitators (ESPs) and fabric filters (FF), the latter sometimes referred to as baghouses.

Several control strategies have been developed for the control of mercury emissions from coal-fired boilers. Some of these methods include injection of activated carbon, modified activated carbon, various chemical catalysts, and inorganic sorbents. Unfortunately, none of these strategies removes all the mercury from the flue gas. The efficiencies range from as low as 30% to as high as 80% based on the amount of mercury entering the system with the coal. In addition, these technologies either produce unwanted effects on by-products such as impacting the quality of fly ash, or they generate additional waste streams for the power plant. Both lead to higher operational costs for the power plant. One promising strategy is to take advantage of existing air pollution control devices (APCDs) to augment or to serve as the primary means to remove vapor-phase mercury. Two examples of APCDs are semi-dry and wet scrubbers or flue gas desulfurizers (FGD). Semi-dry FGDs are also known as spray dryer absorbers (i.e., SDAs), circulating dry scrubbers (CDS), or TURBBOSORP® available from Von Roll.

Sulfur oxides ($SO_x$) regulatory compliance mandates the use of at least one of several control strategies. Three such strategies that are used in the US are sorbent injection into the flue gas following by a particulate collection device such as an ESP or a FF, and wet or dry flue gas desulfurizers. At present, about 3% of the coal-fired power plants are using sorbent injection. FGD scrubbing accounts for 85% using wet and 12% using dry scrubber technologies. Wet scrubbers achieve greater than 90% $SO_x$ removal efficiency compared to 80% by dry scrubbing. In wet scrubbers, the flue gas is brought into contact with slurry containing an alkaline source such as lime or limestone. The $SO_x$ is adsorbed into the water and reacts to form calcium sulfite. It has been demonstrated that simultaneous to $SO_x$ capture, wet FGDs can be used to capture vapor-phase mercury from the flue gas.

Elemental mercury is water-insoluble and is not removed by a wet FGD. In contrast, oxidized mercury in the flue gas is water-soluble and is removed. The Information Collection Request (ICR) mercury data demonstrated that ionic mercury is removed effectively approaching 90% by wet FGDs. Hence, one strategy for mercury capture is to oxidize all the mercury during the burning of the coal and capture the oxidized mercury in the wet scrubber. Work carried out by URS in conjunction with the Department of Energy/National Energy Technology Laboratory (DOE/NETL) investigated just such a strategy. There are two critical technical steps to the implementation of this strategy. The first is the complete oxidation of the vapor-phase mercury exiting the boiler and the coal. URS, among others, is developing strategies and technologies to accomplish this step. To date, they have demonstrated that independent of the coal type, vapor-phase mercury speciation can be shifted to extensively 100% oxidized mercury. The second critical technical step in the implementation of this control strategy is the sorption of the oxidized mercury and removal in the wet scrubber. The problem, identified early on, is that there are reactions occurring in the wet scrubber liquor that reduce oxidized mercury to elemental mercury and lead to "re-emission" or release of elemental mercury into the scrubbed flue gas. The prevention of ionic mercury reduction in wet scrubber liquor has been studied and reported by G. M. Blythe and D. W. DeBerry at URS and others.

The findings have suggested that complexation of the ionic mercury is one way to reduce or eliminate the generation of elemental mercury in the scrubber. This same study has demonstrated that not all chelants of ionic mercury can accomplish this in a wet FGD. In a recent presentation, plant results of such a chelant, TMT-15, trimercapto-s-triazine, available from Degussa, were inconclusive regarding the prevention of re-emission of mercury across a wet scrubber. Efficient and cost-effective apparatuses and methods for controlling emissions of mercury remain a desirable need in the art whether from combustion sources such as coal plants and cement kilns or other sources such as incinerators used in a variety of activities.

SUMMARY

In one aspect, a method for reducing mercury emissions is disclosed. In one embodiment, the method includes providing a gas stream comprising mercury and passing the gas stream into a scrubber comprising a scrubber liquor and peracetic acid.

In one embodiment, the method includes burning a carbonaceous fuel comprising mercury, thereby producing a flue gas, and passing the flue gas into a flue gas scrubber comprising a scrubber liquor and peracetic acid.

In some embodiments, the peracetic acid is mixed with a carrying agent selected from: limestone slurry, lime slurry, sodium-based alkali solution, trona-based solution, sodium carbonate solution, sodium hydroxide solution, and water.

In some embodiments, the method also includes mixing acetic acid and an oxidant to form the peracetic acid. In some embodiments, the oxidant is selected from hydrogen peroxide, sodium hypochlorite and mixtures of the same. In some embodiments, the oxidant is hydrogen peroxide.

In some embodiments, the mercury is from combusted coal. In some embodiments, the mercury is from an incinerator. In some embodiments, the mercury is from a cement kiln. In some embodiments, the mercury is from an ore refinery. In some embodiments, the mineral ore processed at the refinery contains phosphorus (such as phosphate). In some embodiments, the mineral ore processed at the refinery contains gold.

In some embodiments, the scrubber is a wet scrubber selected from a spray tower system, a jet bubbler system, and a co-current packed tower system. In some embodiments, the peracetic acid is added to the liquor and then added to the scrubber. In some embodiments, the peracetic acid is added to the scrubber containing the liquor. In some embodiments, the peracetic acid is added to a virgin liquor then added to the scrubber. In some embodiments, the peracetic acid is added to a make-up liquor then added to the scrubber. In some embodiments, the peracetic acid is added to a return liquor then added to the scrubber. In some embodiments, the peracetic acid is added to a reclaimed liquor then added to the scrubber. In some embodiments, the peracetic acid is added to a liquor injected directly into flue gases then added to the scrubber. In some embodiments, the peracetic acid is added to a recirculation loop of the scrubber liquor. In some embodiments, the peracetic acid is added to a low solids return to the scrubber from a scrubber purge stream. In some embodiments, the peracetic acid is added to a demister. In some embodiments, the peracetic acid is added to a make-up water stream.

DETAILED DESCRIPTION

Figure 1:
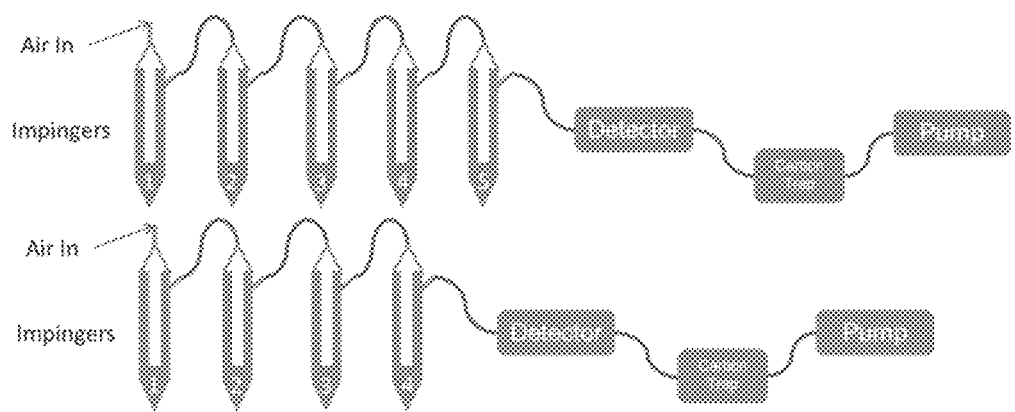
FIG. 1 shows a schematic of an experimental setup of impingers to measure simulated mercury emission capture.

Unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

The present invention describes the use of peracetic acid to unexpectedly improve the capture of mercury emissions across a flue gas desulfurizer (FGD) in coal-fired flue gas streams or other processing system where mercury vapor is present or released. Examples include municipal solid waste (MSW) incinerators, medical waste combustors, ore roaster and refineries and cement kilns.

The scrubbers currently used in the industry include spray towers, jet bubblers, and co-current packed towers as examples. These types of air pollution control devices (APCDs) are provided as examples and are not meant to represent or suggest any limitation. The peracetic acid may be added to virgin limestone or lime slurry prior to addition to the scrubber, the recirculation loop of the scrubber liquor, the "low solids" return to the scrubber from the scrubber purge stream, demister water, make-up water, or the scrubber liquor. Semi-dry FGDs can also be adapted, including spray dryer absorbers (i.e., SDAs), circulating dry scrubbers (CDS) or TURBBOSORP® available from Von Roll. The peracetic acid may be added to semi-dry FGDs so that the peracetic acid contacts mercury passing through the scrubber.

Typically, the peracetic acid is applied at a ratio of 0.5:1 to 20000000:1 weight peracetic acid to weight of mercury being captured. The preferred ratio is from 1:1 to 2000000:1 and the most preferred range is from 5:1 to 200000:1.

In some embodiments, the peracetic acid is generated by mixing acetic acid with an oxidant source. The oxidant source may be any agent capable of converting the acetic acid to peracetic acid. Examples of appropriate oxidant sources include hydrogen peroxide and sodium hypochlorite.

In general, peracetic acid may be introduced into the scrubber and thereby into the scrubber liquor via several routes. The following will serve as just some of the variations that are available to introduce the peracetic acid into the scrubber liquor. The scrubber liquor is defined as the water-based dispersion of calcium carbonate (limestone) or calcium oxide (lime) used in a wet or dry flue gas scrubber to capture $SO_x$ emissions. The liquor may also contain other additives such as magnesium and low-molecular weight organic acids, which function to improve sulfur capture. One example of such an additive is a mixture of low-molecular weight organic acids known as dibasic acid (DBA). DBA typically consists of a blend of adipic, succinic, and glutaric acids. Each of these organic acids can also be used individually. In addition, another low-molecular weight organic acid that can be used to improve sulfur capture in a wet scrubber is formic acid. Finally, the scrubber liquor will also contain byproducts of the interaction between the lime or limestone and flue gas, which leads to the presence of various amounts of calcium sulfite or calcium sulfate as well as anions such as halides (i.e., chlorides, bromides, and iodides) and other cations such as iron, zinc, sodium, or copper. The scrubber liquor includes but is not limited to the make-up liquor, return liquor, the reclaimed liquor, virgin liquor, and liquor injected directly into flue gases.

Another addition point for the peracetic acid to the wet scrubber is via the "low solids" liquor return. A portion of the liquor is usually continuously removed from the scrubber for the purpose of separating reaction byproducts from unused lime or limestone. One means of separation that is currently used is centrifugation. In this process the scrubber liquor is separated into a "high solids" and "low solids" stream. The high solids stream is diverted to wastewater processing. The low solids fraction returns to the wet scrubber and can be considered reclaimed dilute liquor. The peracetic acid can conveniently be added to the reclaimed low solids stream prior to returning to the scrubber.

Another feed liquor found in the operation of a wet FGD is called "virgin liquor." Virgin liquor is the water-based dispersion of either lime or limestone prior to exposure to flue gas and is used to add fresh lime or limestone while maintaining the scrubber liquor level and efficiency of the wet FGD. This is prepared by dispersing the lime or limestone in water. Here, the peracetic acid can be added either to the dispersion water or the virgin liquor directly or to the demister water.

Finally, some scrubber installations use scrubber liquor and/or water (fresh or recycled) injected directly into the flue gas prior to the scrubber for the purpose of controlling relative humidity of the flue gas or its temperature. The excess liquid is then carried into the scrubber. Here also are two potential addition points for the introduction of the peracetic acid.

The addition of the peracetic acid can be made in any of these locations, wholly or fractionally (i.e., a single feed point or multiple feed points), including, but not limited to, the make-up water for the lime or limestone slurry or the scrubber liquor.

Often, the recovery of desirable ore products involves refining the ore from materials that contain mercury. For example, phosphate is often extracted from phosphorite which contains mercury as a trace element. During refinement of the desirable phosphorous mineral, mercury can be liberated such during fertilizer manufacture. In such cases, the mercury passes into a scrubber fluid, for example, a sodium-based alkali that is used to capture sulfur dioxide ($SO_2$). The mercury can be removed using the processes described herein.

As another example, gold ore processing often involves roasting the gold ore to oxidize and remove sulfide. The gas generated by sulfur burning in the roaster is scrubbed to remove the sulfur dioxide and other components which can be contaminated with mercury. Mercury can be removed from these off-gases to make the gold processing more environmentally desirable.

Thus, techniques described herein can be used to remove contaminating amounts of mercury from off-gases arising from various ore processing and ore refineries processing those ores.

The invention is illustrated by the proceeding descriptions and the following examples which are not meant to limit the invention unless otherwise stated in the claims appended hereto.

EXAMPLES

Testing for elemental mercury oxidation or absorption was performed using a multiple impinger setup with an inline mercury analyzer. The inline mercury analyzer for this testing was an Ohio Lumex RA-915 Portable Zeeman Mercury Analyzer.

Referring to FIG. 1, a multiple impinger setup (with impingers serially connected: 1 to 2, 2 to 3, 3 to 4, etc.) was used to expose samples with elemental mercury. In Impinger 1, elemental mercury was added (200 ppt, 5 mL) and combined with stannous chloride (2 mL) to evolve elemental mercury. In Impinger 2, 30 mL of solution was added. The solution can be a diluted sample, synthetic slurries, test slurries, deionized (DI) water (for calibration and reference) or any combination of the above. In Impingers 3-4, various solutions (30 mL) were added to reduce the amount of volatile material reaching the detector and not affect the mercury signal. These various solutions included $HNO_3$ and NaOH solutions at concentrations from 0.1 to 1M. During calibration, these materials are replaced with the same volume of DI water. In the last impinger—Impinger 3, 4, or 5, depending on the system—was left empty to catch any liquid overflow. The mercury detector was then connected to the last impinger, followed by a carbon trap and pump. The pump draws ambient air from the room where the impingers are located.

The second impinger used for this application was not a typical bottom draining impinger. Instead, a 100 mL round bottom flask was fitted at the bottom of the impinger so that the flask could be lowered into a heating bath for variable temperature measurements and was large enough for a variety of test solution volumes. The solution was bubbled with gas through a disposable pipette.

Test slurries used were obtained from a commercial limestone forced oxidation wet flue gas desulfurization scrubber at a coal-fired electrical generator unit firing eastern bituminous coal. The pH of the slurry is typically between 5.5 and 6.5.

Example 1

Figure 2:
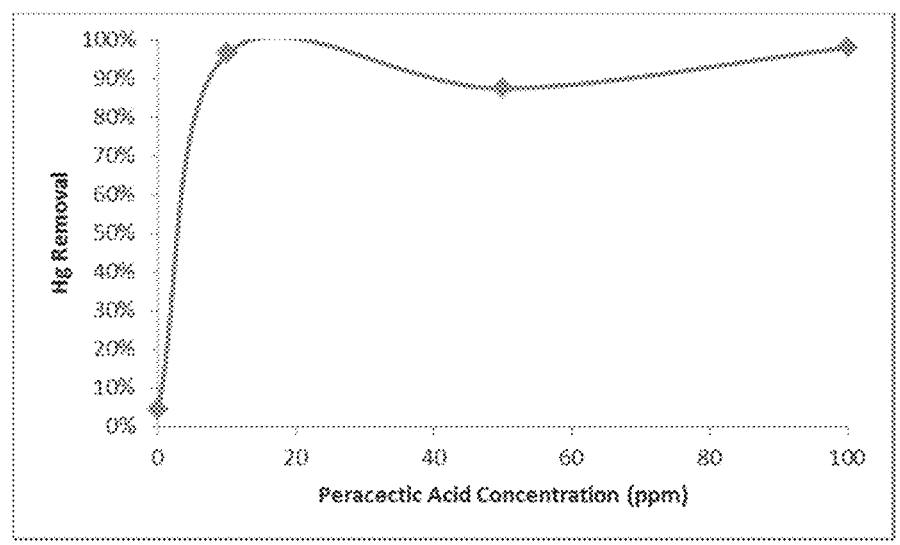
FIG. 2 shows the percentage of mercury removed from a flue gas using an embodiment of the invention at various peracetic acid concentrations.

Peracetic acid was tested as an additive to a test slurry. FIG. 2 shows that the addition of peracetic acid to the test slurry drastically increases the amount of flue gas elemental mercury captured by the water-based liquor.

Mercury removal in FIG. 2 is calculated using the amount of elemental mercury not captured ($[Hg^0]_{NC}$, mercury detected at the detector) compared to the amount of mercury initially in the system ($[Hg^0]_I$ (Equation 1).

$$\text{Hg Removal}(\%) = \left(1 - \frac{[Hg^0]_{NC}}{[Hg^0]_I}\right) \times 100 \quad \text{(Equation 1)}$$

Comparative Example 1

Peroxysulfonated oleic acid was also added to the test slurry but resulted in mercury evolving from the solution (data not shown).

Comparative Example 2

To test the saturation of elemental mercury in water, a known amount of elemental mercury vapor was bubbled through deionized water in a plastic jug using a Mercury Instruments MC-3000 Mercury Calibrator. A mercury generator was employed to create vapor phase elemental mercury (29 or 270 μg/m$^3$) with a $N_2$ carrier gas (2.5 L/min). This gaseous mixture was then bubbled through deionized water (0.9 L) for a varying amount of time (1-20 min). A small amount of water was then removed for analysis on an Ohio Lumex RA-915 Portable Zeeman Mercury Analyzer.

The retention of elemental mercury in water over time was also tested using the same testing setup and procedure as above with one addition. After bubbling mercury through the deionized water for a set amount of time, the mercury ampule was bypassed so that only $N_2$ gas would flow through the deionized water.

Elemental mercury was bubbled through deionized water to determine the saturation of elemental mercury in a system more similar to the dynamic system in a wet flue gas desulfurizer scrubber. The results shown in Table I indicate that the system was driving towards a steady state of ~60 ppt and ~700 ppt, at 29 μg/m$^3$ and 270 μg/m$^3$ respectively, rather than increasing up to the saturation limit of 60 ppb (60,000 ppt) all at 25° C. The initial concentrations at short times are higher than expected due to an oversaturation of the nitrogen carrier gas in the head space of the mercury ampule, causing a burst of elemental mercury at the beginning of each test. Over time in both the low and high concentration systems, the concentration of elemental mercury drives to an equilibrium value. The theoretical values in Table I refer to the total amount of elemental mercury flow through the testing system based on concentration, flow rate and time.

TABLE I

| Gas: 29 μg/m$^3$ and 2.5 L/min | | | Gas: 270 μg/m$^3$ and 2.5 L/min | | |
|---|---|---|---|---|---|
| Elapse Time | Hg$^0$ in water, (ppt) | | Elapse Time | Hg$^0$ in water, (ppt) | |
| (min) | Theoretical* | Actual | (min) | Theoretical* | Actual |
| 1.0 | 146 | 235 | 1 | 349 | 601 |
| 2.5 | 309 | 137 | 10 | 6,139 | 701 |
| 5.0 | 521 | 93 | 20 | 21,139 | 667 |
| 10.0 | 937 | 61 | | | |
| 15.0 | 1,342 | 58 | | | |

The saturation of elemental mercury in water was driving to equilibrium as governed by Henry's Law (Equation 2 below). Henry's law is defined as Henry's constant ($K_H$, 376 atm at 25° C.), mole fraction of elemental mercury in solution (x), and partial pressure of elemental mercury (p, atm). Below in Table II are the theoretical values of elemental mercury in water based on Henry's Law and the concentration of the gas flowing through the system. The values are not exactly the same as the actual measured values but are on the same order of magnitude. These predictions are significantly lower than the solubility limit of 60 ppb for elemental mercury in pure water.

$$K_H = \frac{p}{x} \qquad \text{Equation 2}$$

TABLE II

| Elemental Mercury Concentration | | |
|---|---|---|
| Gas Phase | Water Phase (ppt) | |
| (μg/m$^3$) | Actual | Theoretical* |
| 29 | 60 | 103 |
| 270 | 700 | 963 |
| 0.3 | — | 2 |
| 5.0 | — | 18 |
| 16,823 | — | 60,000 |

Next, these same solutions were tested for mercury retention or stability by first adding elemental mercury to the water in the same manner as above and then bypassing the elemental mercury ampoule so that only $N_2$ gas (elemental mercury content of zero) bubbles through the water for a varying amount of time. This would approximate the effect of a forced oxidation system in the wet flue gas desulfurizer scrubbers. In Table III, it can be seen that the elemental mercury was quickly removed from the deionized water by the pure $N_2$ gas. This behavior is also consistent with Henry's Law as the elemental mercury in the water phase transfers to the gas phase, the system continuously shifts in order to reach equilibrium. Elemental mercury was not readily soluble or retained in deionized water.

TABLE III

| 29 μg/m$^3$ at 2.5 L/min for 1 min | | | 270 μg/m$^3$ at 2.5 L/min for 1 min | | |
|---|---|---|---|---|---|
| $N_2$ flow time (min) | Hg (ppt) | % retention | $N_2$ flow time (min) | Hg (ppt) | % retention |
| 0 | 297 | | 0 | 601 | |
| 1 | 174 | 59% | 1 | 374 | 62% |
| 2.5 | 71 | 24% | 2.5 | 157 | 26% |
| 5 | 14 | 5% | 5 | 35.7 | 6% |

| 29 μg/m$^3$ at 2.5 L/min for 10 min | | | 270 μg/m$^3$ at 2.5 L/min for 10 min | | |
|---|---|---|---|---|---|
| $N_2$ flow time (min) | Hg (ppt) | % retention | $N_2$ flow time (min) | Hg (ppt) | % retention |
| 0 | 76 | | 0 | 701 | |
| 1 | 46 | 61% | 1 | 439 | 63% |
| 2.5 | 18 | 24% | 5 | 90 | 13% |
| 5 | 3.4 | 4% | 10 | 5.4 | 1% |

The data in these tables clearly define the problem by demonstrating that water-based scrubber liquors do not effectively decrease elemental mercury concentration in combustion flue gas.

These bench-scale results shown in Table IV and FIG. 2 demonstrate that the peracetic acid compound successfully and unexpectedly controls the emission of mercury from a scrubber by decreasing the elemental mercury flue gas concentration and does so more efficiently than conventional techniques.

TABLE IV

| Peracetic Acid (ppm) | Elemental Mercury Retention (%) | Activated Carbon (ppm) | Elemental Mercury Retention (%) |
|---|---|---|---|
| 100 | 98% | 100 | 12% |
| 50 | 88% | — | — |

TABLE IV-continued

| Peracetic Acid (ppm) | Elemental Mercury Retention (%) | Activated Carbon (ppm) | Elemental Mercury Retention (%) |
|---|---|---|---|
| 10 | 97% | — | — |
| 0 | 5% | — | — |

Example 2

Using an experimental reticulating slurry system, elemental mercury (~11 μg/m$^3$ in N$_2$) was bubbled through a 1 L solution of deionized water or WFGD slurry sample from a power plant in a large impinger. Peracetic acid was added at a rate of 50 ppm/hour to the basin of the system which fed area being fed to the impinger. Elemental mercury was continuously monitored at the output of the system. To the elemental mercury gas stream SO$_2$ was also added at 100 ppm for some tests.

TABLE V

| SO$_2$ Concentration (ppm) | Elemental Mercury Removal (%) | |
|---|---|---|
| | DI water | WFGD Slurry |
| 0 | 0% | 32% |
| 100 | 64% | 91% |

Table V includes data from peracetic acid addition to deionized water and slurry at 50 ppm/hour. Included is data with and without SO$_2$ incorporated into the elemental mercury gas stream.

The presence of SO$_2$ in the elemental mercury gas stream of solutions containing peracetic acid for elemental mercury removal see a synergistic increase in elemental mercury removal. Even in systems where no elemental mercury removal was previously seen (DI water), the addition of SO$_2$ to the gas stream greatly increased the amount of elemental mercury removed by systems containing peracetic acid.

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method for reducing mercury emissions, comprising: providing a gas stream comprising mercury;
passing the gas stream into a scrubber comprising a scrubber liquor, peracetic acid, and hydrogen peroxide, wherein the peracetic acid is mixed with a carrying agent selected from the group consisting of a lime slurry, a sodium-based alkali solution, a trona-based solution, a sodium carbonate solution, a sodium hydroxide solution, water, and any combination thereof, and
removing the mercury from the gas stream,
wherein the peracetic acid is applied at a ratio of 5:1 to 200000:1 weight the peracetic acid to weight of the mercury being captured.

2. The method of claim 1, wherein the carrying agent is water.

3. The method of claim 1, wherein the mercury is from combusted coal.

4. The method of claim 1, wherein the scrubber is a wet scrubber selected from a spray tower system, a jet bubbler system, and a co-current packed tower system.

5. The method of claim 1, wherein the peracetic acid is added to the liquor and then added to the scrubber.

6. The method of claim 1, wherein the peracetic acid is added to the scrubber containing the liquor.

7. The method of claim 1, wherein the peracetic acid is added to a virgin liquor then added to the scrubber.

8. The method of claim 1, wherein the peracetic acid is added to a make-up liquor then added to the scrubber.

9. The method of claim 1, wherein the peracetic acid is added to a return liquor then added to the scrubber.

10. The method of claim 1, wherein the peracetic acid is added to a reclaimed liquor then added to the scrubber.

11. The method of claim 1, wherein the peracetic acid is added to a liquor injected directly into flue gases then added to the scrubber.

12. The method of claim 1, wherein the peracetic acid is added to a recirculation loop of the scrubber liquor.

13. The method of claim 1, wherein the peracetic acid is added to a low solids return to the scrubber from a scrubber purge stream.

14. The method of claim 1, wherein the peracetic acid is added to an aqueous stream introduced into the scrubber, wherein the aqueous stream is selected from a demister and make-up water stream.

15. The method of claim 1, wherein the mercury is from an incinerator, cement kiln, or an ore refinery.

16. The method of claim 1, wherein the peracetic acid is not added directly to the scrubber.

17. The method of claim 1, wherein the peracetic acid is added in an amount of about 10 ppm to about 100 ppm.

* * * * *